US012150687B2

(12) United States Patent
Diao et al.

(10) Patent No.: US 12,150,687 B2
(45) Date of Patent: Nov. 26, 2024

(54) CRYOABLATION CATHETER AND SYSTEM (71) Applicant: CRYOFOCUS MEDTECH (SHANGHAI) CO., LTD., Shanghai (CN)

(72) Inventors: Yuepeng Diao, Shanghai (CN); Donghui Yang, Shanghai (CN); Pan Li, Shanghai (CN)

(73) Assignee: CyroFocus MedTech (Shanghai) Co., Ltd., Shanghai (CN)

( * ) Notice: Subject to any disclaimer, the term of this patent is extended or adjusted under 35 U.S.C. 154(b) by 596 days.

(21) Appl. No.: 16/646,843

(22) PCT Filed: Aug. 30, 2018

(86) PCT No.: PCT/CN2018/103237
§ 371 (c)(1),
(2) Date: Mar. 12, 2020

(87) PCT Pub. No.: WO2019/052342
PCT Pub. Date: Mar. 21, 2019

(65) Prior Publication Data
US 2021/0077173 A1 Mar. 18, 2021

(30) Foreign Application Priority Data
Sep. 12, 2017 (CN) .......................... 201710816282.6

(51) Int. Cl.
*A61B 18/02* (2006.01)
*A61B 18/00* (2006.01)
(52) U.S. Cl.
CPC .... *A61B 18/02* (2013.01); *A61B 2018/00255* (2013.01); *A61B 2018/00577* (2013.01);
(Continued)

(58) Field of Classification Search
CPC ...................... A61B 18/02; A61B 2018/00255
See application file for complete search history.

(56) References Cited

U.S. PATENT DOCUMENTS 5,334,181 A * 8/1994 Rubinsky ............... A61B 18/02
606/26
5,807,310 A * 9/1998 Hood .................. A61F 9/00745
606/107
(Continued)

FOREIGN PATENT DOCUMENTS

CN 104427949 3/2015
CN 106102816 11/2016
(Continued)

OTHER PUBLICATIONS

Supplementary European Search Report for related European Application No. EP18855833.2 dated Dec. 15, 2020.
(Continued)

*Primary Examiner* — Daniel W Fowler
(74) *Attorney, Agent, or Firm* — Syncoda LLC; Feng Ma (57) ABSTRACT

The disclosure relates to a cryoablation catheter and a cryoablation system. The cryoablation catheter comprises a catheter body and a freezing unit. The catheter body comprises a cold-source fluid input lumen and a cold-source fluid output lumen, both extending in an axial direction of the catheter body, and the freezing unit is arranged at a distal portion of the catheter body, and comprises a first balloon in fluid communication with the cold-source fluid input lumen and the cold-source fluid output lumen, and a second balloon arranged external to the first balloon with the length of the first balloon being less than the length of the second balloon. When the first balloon and the second balloon are dilated, a cavity is formed between the first balloon and the second balloon, to prevent the energy transfer in a space of the freezing unit corresponding to the cavity.

5 Claims, 7 Drawing Sheets

(52) U.S. Cl.
CPC ................ *A61B 2018/0212* (2013.01); *A61B 2018/0262* (2013.01)

(56) References Cited

U.S. PATENT DOCUMENTS

| | | | |
|---|---|---|---|
| 6,758,847 B2 * | 7/2004 | Maguire | A61N 7/02 606/41 |
| 6,832,998 B2 * | 12/2004 | Goble | A61B 18/14 606/50 |
| 2002/0007180 A1 | 1/2002 | Wittenberger et al. | |
| 2002/0045893 A1 * | 4/2002 | Lane | A61B 18/02 606/21 |
| 2009/0088735 A1 | 4/2009 | Abboud et al. | |
| 2009/0182317 A1 * | 7/2009 | Bencini | A61B 18/02 606/21 |
| 2009/0234345 A1 * | 9/2009 | Hon | A61B 18/02 606/21 |
| 2009/0299356 A1 * | 12/2009 | Watson | A61M 25/1006 606/21 |
| 2010/0100087 A1 | 4/2010 | Mazzone et al. | |
| 2010/0324546 A1 | 12/2010 | Levin et al. | |
| 2011/0184400 A1 * | 7/2011 | Pageard | A61B 18/02 606/21 |
| 2011/0190751 A1 * | 8/2011 | Ingle | A61B 18/02 606/21 |
| 2012/0143131 A1 * | 6/2012 | Tun | A61M 25/10 604/101.02 |
| 2013/0165914 A1 | 6/2013 | Satake | |
| 2014/0276706 A1 | 9/2014 | Duong et al. | |
| 2014/0358137 A1 | 12/2014 | Hu | |
| 2015/0250525 A1 | 9/2015 | Ingle et al. | |
| 2015/0250991 A1 | 9/2015 | Silvestro | |
| 2015/0289920 A1 * | 10/2015 | Burnett | A61B 18/02 606/26 |
| 2016/0262823 A1 * | 9/2016 | Aklog | A61B 18/04 |

FOREIGN PATENT DOCUMENTS

| | | |
|---|---|---|
| CN | 106691676 | 5/2017 |
| CN | 107411815 | 12/2017 |
| EP | 1301133 | 11/2005 |
| JP | 2004504098 A | 2/2004 |
| WO | WO 02/07628 | 1/2002 |
| WO | WO 03/020334 | 3/2003 |
| WO | WO2010/083281 | 7/2010 |
| WO | WO2017/047545 | 3/2017 |

OTHER PUBLICATIONS

English abstract of CN104427949.
English abstract of CN106102816.
English abstract CN106691676.
English abstract of CN107411815.
English abstract of WO2017047545.
International Search Report for related PCT Application No. PCT/CN2018/103237 dated Nov. 22, 2018.
English abstract of JP2004504098.
Notice of Reasons for Refusal for corresponding Japanese Patent Application No. JP2020-535287, dated Apr. 8, 2021.

* cited by examiner

CRYOABLATION CATHETER AND SYSTEM

CROSS-REFERENCE TO RELATED APPLICATIONS

This application is a U.S. National Phase Application under 35 U.S.C. § 371 of PCT/CN2018/103237, filed Aug. 30, 2018, which claims priority to Chinese Patent Application No. 201710816282.6, filed Sep. 12, 2017, the contents of which applications are incorporated by reference herein in their entireties.

TECHNICAL FIELD

The present disclosure relates to the field of cryoablation medical device, and particularly relates to a cryoablation catheter and system.

BACKGROUND

Cryoablation refers to destroying cells by freezing the cells into an ice ball both inside and outside by using a low temperature. In cryoablation, a cryoprobe is placed at the surface of the tissue, and the low temperature is generated by refrigeration, to cause the cells adjacent to the probe to form an ice ball both inside and outside. With the decreasing of the temperature, the cells in the ice ball suffer from irreversible damage. The damage process of cryoablation may be divided into three stages: (1) freezing/thawing period; (2) bleeding and inflaming period; and (3) fibrosis period.

Cryoablation is a useful treatment in extensive catheter-based interventional surgery. For example, cryoablation can be used to ablate the vestibule of pulmonary vein, to cause the electrical isolation of the pulmonary vein, thereby treating atrial fibrillation. Cryoablation can be used to ablate the sympathetic nerve of renal artery, thereby treating resistant hypertension, for which the technique has already been used for clinical trial. Cryoablation can also be used to ablate tumours, to treat arterial hemadostenosis and so on. In those cryotherapy processes, the refrigerant may be delivered by pushing dilatable balloons through human body lumens. Those balloons are operably connected to an in-vitro manipulating component (such as a refrigerant source). With the increasingly extensive application of surgical intervention cryotherapy, the innovation of the relative apparatuses, systems and methods is required (for example, regarding the efficacy, the safety, the efficiency and/or the reliability). Such innovation may probably further expand the function of cryotherapy as a tool for improving patients' health. The conventional cryoablation catheters mostly deliver the freezing unit at the distal end of the catheters to the treatment position, and perform freezing.

As a representative of frozen balloon catheters, the Arctic Front product of the Medtronic Company and its subsequent improved models entered the Chinese market in 2013. The product is placed to against an ostia of pulmonary vein by a filled balloon, and when a liquid refrigerant ($N_2O$) is sprayed into the balloon and gasified, the liquid refrigerant absorbs a great amount of heat, to reduce the temperature of the target site to be ablated to realize the ablation. Clinical data indicated that the effectiveness of the Medtronic products is obvious, wherein the rate of success for one year is 69.90%. However, because no cavity for preventing energy transfer exists between the first balloon and the second balloon, the freezing energy can spread, which, besides ablating the target site (the vestibule of the pulmonary vein), affects the peripheral tissues, such as the phrenic nerves, the vagus nerves, the esophagus, the bronchus and so on. The freezing energy effects on the peripheral tissues, which causes the related complications, such as phrenic nerve paralysis, vagus nerve injury and esophageal fistula. It is reported that when the Arctic Front Advance of Medtronic is used for pulmonary vein ablation, the incidence of phrenic nerve paralysis is up to 13.5%.

The Chinese patent CN201710096224.0 discloses a thermally insulated device for protecting esophagus in the frozen balloon catheter cryoablation process of pulmonary veins. A balloon wall thermocouple, an intra balloon thermocouple and a thermal circulating insulation device are arranged in a balloon, and the balloon wall thermocouple and the intra balloon thermocouple are respectively attached onto the inner wall and the outer wall of the balloon to measure the temperature in real time, and the thermal circulating insulation device is connected with a heat insulation module, and a temperature controlling module is connected with the balloon wall thermocouple, the intra balloon thermocouple and the heat insulation module are used for controlling and feeding back the temperature of the balloon, and controlling the cold and heat amount of the thermal circulating insulation device by intelligent match, so as to keep the temperature of a pulmonary vein ablation area near the esophagus at 20-30. The thermally insulated device provided by the invention can be introduced to the cryoablation area through the esophagus natural cavity, and the heat insulation balloon is used in the cryoablation process of the pulmonary vein so as to protect the esophagus near the cryoablation area of the pulmonary vein, prevent esophageal fistula and other serious damages caused by cryoablation, and eliminate the limitations of cryoablation treatment of pulmonary vein on atrial fibrillation by using frozen balloon catheters, and facilitate the popularization and promotion of the ablation of pulmonary vein by using frozen balloon catheters. However, the heat insulation device need many components, has a complicated structure. Thus, it is merely suitable for the treatment of the particular target tissue, and has a high cost.

Although conventional cryoablation catheters employ fixing the inner and outer two-layer balloons to the catheter rod, and realize refrigeration by filling refrigerant fluid into the inner balloon, because no effective thermal insulation cavity exists, the formed ice ball often covers the periphery areas of the treatment position, which hurts the peripheral tissues, and results in complications.

SUMMARY

In view of the above defects of the prior art, the technical problem that the present application seeks to solve is to provide a cryoablation catheter and system having a heat insulation cavity, wherein the catheter and system can effectively restrict the freezing energy release area so as to reducing the probability of complications, and has wide application.

A technical solution that is employed by the present application to solve its technical problem is:

A cryoablation catheter, comprising:

a catheter body, wherein the catheter body comprises a cold-source fluid input lumen and a cold-source fluid output lumen, both extending in an axial direction of the catheter body; and a freezing unit arranged at a distal portion of the catheter body, wherein the freezing unit comprises a first balloon in fluid communication with the cold-source fluid input lumen and the cold-source fluid output lumen and a second balloon arranged external to the first balloon with the length of the first balloon being less than the length of the second balloon, an area between the first balloon and the second balloon is a sealed space, a part of wall of the first balloon and a part of wall of the second balloon are fitted, and the joint portion of the walls of the first balloon and of the second balloon is a channel for transferring freezing energy to a treatment position, wherein when the first balloon and the second balloon are dilated, a cavity for preventing energy transfer is formed between the first balloon and the second balloon, to prevent energy transfer in the space of the freezing unit corresponding to the cavity.

Further technical solutions that are employed by the present application to solve its technical problem are:

In an embodiment, the cavity is pre-filled with a heat insulation fluid, so as to prevent energy transfer inside the cavity.

In an embodiment, a supporting structure is provided between the first balloon and the second balloon, and when the first balloon and the second balloon are dilated, the supporting structure is able to support the cavity for preventing energy transfer formed between the first balloon and the second balloon, to enable a shape of the cavity for preventing energy transfer to be stable and reliable.

In a preferable embodiment, the supporting structure is a balloon, the catheter body further comprises a balloon filling lumen extending in an axial direction of the catheter body, and the balloon filling lumen is in fluid communication with the balloon.

In a preferable embodiment, the supporting structure is made of one or more shape-memory-alloy wires having a preset shape, and the shape-memory-alloy wires are arranged between the first balloon and the second balloon.

In a preferable embodiment, the supporting structure is a protrusion arranged on the first balloon.

In a preferable embodiment, the supporting structure is a wrinkle arranged at a proximal end and/or a distal end of the first balloon.

In a preferable embodiment, the wrinkle is formed by directly stacking the first balloon.

In a preferable embodiment, the supporting structure is formed by a plurality of ribbon-like or wire-like structures, both ends of the ribbon-like or wire-like structures are fixedly connected to two ends of the second balloon respectively, and when the first balloon and the second balloon are dilated, the ribbon-like or wire-like structures are tightened, thereby forming the cavity for preventing energy transfer between the first balloon and the second balloon.

In a preferable embodiment, the cavity is pumped to negative pressure in advance, so as to cause the gas within the cavity to be rarefied, thereby preventing energy transfer.

Another technical solution that is employed by the present application to solve its technical problem is:

A cryoablation system, comprising:

a cryoablation catheter, wherein the cryoablation catheter comprises a catheter body and a freezing unit arranged at a distal portion of the catheter body, and the catheter body comprises a cold-source fluid input lumen, a cold-source fluid output lumen and a filling and sucking lumen those extend in an axial direction of the catheter body; and the freezing unit comprises a first balloon in fluid communication with the cold-source fluid input lumen and the cold-source fluid output lumen, and a second balloon arranged external to the first balloon, the second balloon is in communication with the filling and sucking lumen, the length of the first balloon is less than the length of the second balloon, a part of wall of the first balloon and a part of wall of the second balloon are fitted, and the joint portion of the walls of the first balloon and of the second balloon is a channel for transferring freezing energy to a treatment position; and a cryoablation device, wherein the cryoablation device comprises a heat insulation module and a second thawing module that are in communication with the filling and sucking lumen respectively, a freezing module that is in communication with the cold-source fluid input lumen and the cold-source fluid output lumen, a first thawing module that is in communication with the cold-source fluid input lumen, and a controlling system that controls parameters of the heat insulation module, the freezing module, the first thawing module and the second thawing module, wherein in a cryoablation stage, freezing energy in the freezing module is transferred into the first balloon via the cold-source fluid input lumen, to dilate the first balloon and the second balloon; and the cryoablation system fills the second balloon with a heat insulation medium or sucks the second balloon by using the heat insulation module, to cause the cavity for preventing energy transfer formed between the first balloon and the second balloon to be filled with the heat insulation medium or be pumped to a negative-pressure state, so as to prevent the freezing energy from being transferred via the cavity, and in a thawing stage, the first thawing module and the second thawing module fill a thawing fluid into the first balloon and the second balloon via the cold-source fluid input lumen and the filling and sucking lumen respectively, to enable the freezing unit to be thawed rapidly.

Further technical solutions that are employed by the present application to solve its technical problem are:

In an embodiment, the heat insulation module is a filling pump.

In an embodiment, the heaty insulation module is a vacuum pump.

In a preferable embodiment, a supporting structure is provided between the first balloon and the second balloon, and when the first balloon is dilated, the supporting structure can support the cavity for preventing energy transfer, to enable a shape of the cavity for preventing energy transfer to be stable and reliable.

In a preferable embodiment, the supporting structure is a balloon, the catheter body further comprises a balloon filling lumen extending in an axial direction of the catheter body, and the balloon filling lumen is in fluid communication with the balloon.

In a preferable embodiment, the supporting structure is made of one or more shape-memory-alloy wires that have a preset shape, one end of the supporting structure is connected to a pushing handle, and when the first balloon has been delivered to a lesion site, the supporting structure is pushed between the first balloon and the second balloon by using the pushing handle.

In a more preferable embodiment, the preset shape comprises spiral shape, cage shape or umbrella shape.

In a preferable embodiment, the supporting structure is formed by a plurality of ribbon-like or wire-like structures, both ends of the ribbon-like or wire-like structures are fixedly connected to two ends of the second balloon respectively, and when the first balloon and the second balloon are dilated, the ribbon-like or wire-like structures are tightened, thereby forming the cavity for preventing energy transfer between the first balloon and the second balloon.

In a preferable embodiment, the supporting structure is a wrinkle arranged at a proximal end and/or a distal end of the first balloon.

In an embodiment, the temperature of the thawing fluid that is injected by the filling and sucking lumen during the thawing stage of the cryoablation system is 0-42 degrees Celsius.

In the above embodiment, a manipulating handle is provided at the proximal end of the catheter body, the manipulating handle is connected to a cold-source connector via a flexible connecting pipe, and the freezing energy in the freezing module is transferred into the first balloon via the cold-source connector, the flexible connecting pipe and the cold-source fluid input lumen provided within the catheter body, to dilate the first balloon.

In a preferable embodiment, at least one connection plug is provided at the proximal end of the cold-source connector, and the distal end of the cold-source connector is connected to the proximal end of the manipulating handle via the flexible connecting pipe.

In the above embodiment, a tip is provided at the farthest distal end of the catheter body. Preferably, the tip is a polymer hose.

In the above embodiment, a guidewire lumen tube is provided within the catheter body, and the distal end of the first balloon is fixedly connected to the guidewire lumen tube.

In a preferable embodiment, the manipulating handle comprises a steerable unit and a guidewire lumen manipulating unit, the steerable unit controls the movement of the distal end of the tip, the guidewire lumen manipulating unit comprises a liquid injecting opening, and the liquid injecting opening is in communication with the lumen of the guidewire lumen tube.

In the above embodiment, a second vacuum lumen is provided external to the catheter body axially along the catheter body.

As compared with the prior art, the advantages and progress of the present application are as follows:

1. The cryoablation catheter of the present application can isolate and prevent energy transfer, and further can limit the release region of the freezing energy, reduce the probability of complications and the cost of treatment, because the heat insulation cavity is arranged at the position of the freezing unit where energy transfer is not expected. Furthermore, depending on the particular requirements on the protection of the peripheral tissues of different cryoablation areas in different surgeries, the present application can provide one or more cavities for preventing energy transfer at the proximal end or the distal end or any one side or two sides of the freezing unit. Depending on the different requirements on heat insulation of different surgeries, the present application can, inject a heat insulation medium into the cavity or suck the cavity, to enhance the thermally insulated effect, and further to reduce the damage of freezing energy to the peripheral tissue during the surgery.

2. Because of the supporting structure, the cryoablation catheter of the present application can form a more stable and reliable cavity for preventing energy transfer, which does not cause the second balloon to joint to the first balloon under the action of the negative pressure and result in the failure of the heat insulation.

3. The cryoablation system of the present application can isolate energy transfer and prevent thermal transfer by forming the heat insulation cavity through the filling and sucking lumen in the freezing process at the position of freezing unit where energy transfer is not expected, whereby the present application can limit the release region of the freezing energy, reduce the probability of complications, and reduce the cost of treatment. Additionally, the cryoablation system of the present application can accelerate thawing in the thawing process.

4. The present application provides two thawing modules, wherein in a thawing stage, the first thawing module and the second thawing module fill a thawing fluid into the first balloon and the second balloon via the cold-source fluid input lumen and the filling and sucking lumen respectively, to enable the freezing unit to be thawed rapidly.

DETAILED DESCRIPTION OF THE DRAWINGS

In the drawings, 1 is the cold-source connector, 2 is the manipulating handle, 3 is the freezing unit, 4 is the flexible connecting pipe, 5 is the catheter body, 6 is the cavity for preventing energy transfer, 21 is the steerable unit, 22 is the guidewire-lumen manipulating unit, 59 is the same endpoint, 31 is the first balloon, 32 is the second balloon, 33 is the supporting structure, 331 is the balloon, 332 is the shape-memory-alloy wires, 333 is the protrusion, 334 is the wrinkle, 335 is the ribbon-like or wire-like structures, 51 is the cold-source fluid input lumen, 52 is the cold-source fluid output lumen, 53 is the filling and sucking lumen, 54 is the balloon filling lumen, 55 is the tip, 56 is the guidewire lumen tube, 58 is the pushing rod, 531 is the filling and sucking port, 101 is the heat insulation module, 102 is the first thawing module, 102' is the second thawing module, 103 is the freezing module, and 104 is the controlling system.

DETAILED DESCRIPTION

In order to make the purposes, the technical solutions and the advantages of the present application more clear, the present application will be described in detail below by referring to the drawings and the embodiments.

In the present application, proximal end refers to the end that is closer to the surgery operator, and distal end refers to the end that is further away from the surgery operator.

The First Embodiment

Figure 1:
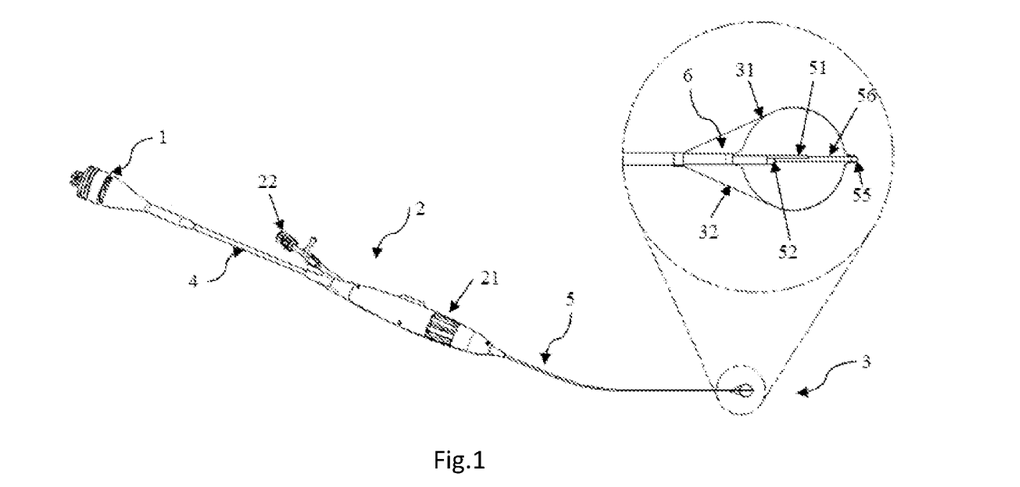
FIG. 1 is a schematic diagram of the overall structure of the cryoablation catheter of the present application.

As shown in FIG. 1, the cryoablation catheter of the present application comprises: a cold-source connector 1, a manipulating handle 2, a freezing unit 3, a flexible connecting pipe 4 and a catheter body 5. The catheter body 5 having a distal end and a proximal end comprises a cold-source fluid input lumen 51 and a cold-source fluid output lumen 52 both extending in an axial direction of the catheter body 5. The freezing unit 3 is arranged at the distal portion of the catheter body 5, and comprises a first balloon 31 that is in fluid communication with the cold-source fluid input lumen 51 and the cold-source fluid output lumen 52, and a second balloon 32 that is arranged external to the first balloon 31. The second balloon 32 dilates along with the first balloon 31. The length of the first balloon 31 is less than the length of the second balloon 32. A part of the wall of the first balloon 31 and a part of the wall of the second balloon 32 are fitted. The joint portion of the walls of the first balloon 31 and of the second balloon 32 is a channel for transferring the freezing energy to a treatment position, the first balloon 31 and the second balloon 32 have a same endpoint 59 at the distal portion of the catheter body. The area between the first balloon 31 and the second balloon 32 is a sealed space, and is pumped to a vacuum state in advance or filled with a certain amount of a heat insulation medium. When the first balloon 31 and the second balloon 32 are dilated, a cavity 6 for preventing energy transfer is formed between the first balloon 31 and the second balloon 32, so as to prevent the energy transfer in the space of the freezing unit 3 corresponding to the cavity 6.

For example, pulmonary vein isolation is a surgical method commonly used for treating atrial fibrillation, and the birth of cryoablation catheters enables pulmonary vein isolation to be more simple and convenient. However, because left atrium has a limited space, and the cryoablated site is limited to merely the vestibule of pulmonary vein, it is desirable to concentrate the freezing energy to the forward hemisphere of the balloon. Therefore, the cavity 6 for preventing energy transfer is arranged at the proximal end of the first balloon 31. In the treatment process, the freezing unit 3 is pushed to the left atrium, and a certain amount of refrigerant is injected into the first balloon 31, whereby the first balloon 31 dilates, and in turn drives the second balloon 32 to dilate. A part of the wall of the first balloon 31 and a part of the wall of the second balloon 32 are fitted. The joint portion of the walls of the first balloon 31 and of the second balloon 32 is a channel for transferring the freezing energy to a treatment position. Because the shapes and the sizes of the first balloon 31 and the second balloon 32 are different, and the cavity 6 for preventing energy transfer is formed between the first balloon 31 and the second balloon 32, so as to prevent the freezing energy from being transferred to the proximal end of the freezing unit 3. Then the freezing unit 3 is pushed to against to the ostia of pulmonary vein to be ablated, and the cryoablation treatment is started up, then a refrigerant is injected into the first balloon 31, thereby absorbing the heat of the treated area so as to reach the effect of cryoablation.

The manipulating handle 2 is arranged at the proximal end of the catheter body 5. The manipulating handle 2 is connected to a cold-source connector 1 via a flexible connecting pipe 4. The cold source is transferred into the first balloon 31 via the cold-source connector 1, the flexible connecting pipe 4 and the cold-source fluid input lumen 51 provided within the catheter body 5, to dilate the first balloon 31. In an embodiment, at least one connection plug is arranged at the proximal end of the cold-source connector 1, and the connection plug is connected to a refrigerating device. The distal end of the cold-source connector 1 is connected to the proximal end of the manipulating handle 2 via the flexible connecting pipe 4, and the refrigerating device provides a refrigerant to the cryoablation catheter via the cold-source connector 1.

In an embodiment, a tip 55 is arranged at the farthest distal end of the catheter body 5. Preferably, the tip 55 is a polymer hose. A guidewire lumen tube 56 is arranged within the catheter body 5, and the tip 55 is fixedly connected to the distal end of the guidewire lumen tube 56 by adhesion or fusion, in order to prevent the cryoablation catheter from damaging blood vessels or tissues during the delivering process. The distal end of the first balloon 31 is fixedly connected to the guidewire lumen tube 56 by processes such as adhesion and welding. The proximal end of the first balloon 31 is fixedly connected to a cold-source circuit by processes such as adhesion and welding. The cold-source circuit comprises the cold-source fluid input lumen 51 and the cold-source fluid output lumen 52. The cold-source circuit may be connected to the refrigerating device via the cold-source connector 1.

The manipulating handle 2 further comprises a steerable unit 21 and a guidewire lumen manipulating unit 22. The steerable unit 21 controls the movement of the distal end of the tip 55. The freezing unit 3 can easily reach the treatment position by controlling a bending shape of the distal end of the tip 55. The guidewire lumen manipulating unit 22 is fixedly connected to the proximal end of the guidewire lumen tube 56. The guidewire lumen manipulating unit 22 comprises a liquid injecting opening in communication with the lumen of the guidewire lumen tube 56, and through which, if necessary, normal saline, a contrast medium or other liquids can be injected.

The way the cryoablation catheter of the present application works is as follows. The freezing unit 3 of the cryoablation catheter is pushed into the target-tissue area, then the first balloon 31 is sufficiently filled, and the second balloon 32 is dilated along with the dilation of the first balloon 31. The cavity 6 for preventing energy transfer is formed between the first balloon 31 and the second balloon 32. The cryoablation catheter is pushed integrally, and the steerable unit 21 is operated, to enable the freezing unit 3 to contact the target tissue. After the above steps have been completed, by operating the refrigerating device, a liquid refrigerant is delivered into the first balloon 31, thereby freezing the target tissue. Because the cavity 6 for preventing energy transfer is formed between the first balloon 31 and the second balloon 32, heat insulation protection is formed at that area, in order to prevent the peripheral tissue being accidentally injured by the freezing energy.

In conventional cryoablation surgeries, because of the conduction of the freezing energy, the areas at the periphery of the target tissue are often refrigerated. The action principle of the cryoablation catheter of the present application is to form the cavity 6 for preventing energy transfer between the first balloon 31 and the second balloon 32, so that the freezing energy does not work on the peripheral areas, thereby forming heat insulation protection. Depending on the particular requirements on the protection of the peripheral tissues of different cryoablation areas in different surgeries, the cavity 6 may also be arranged at the distal end of the first balloon 31, or at both ends of the first balloon 31, or on one side of the first balloon 31. For example, in the cryoablation surgery on atrial fibrillation, the target tissue of cryoablation is the vestibule of the pulmonary vein, and because the front end of the target tissue is adjacent to the phrenic nerve, and the freezing of the phrenic nerve results in phrenic nerve paralysis, therefore, the cavity 6 for preventing energy transfer may be arranged at the distal end of the freezing unit 3. In the cryoablation surgery of the sympathetic nerve of renal artery, the target tissue of cryoablation is the middle and the distal ends of the renal artery. The distal end of the target tissue is adjacent to the renal pelvis, and freezing of the renal pelvis can cause functional impotence. The proximal end of the target tissue is adjacent to the aorta, and improper freezing of the aorta can also results in relative complications. Therefore, the cavity 6 for preventing energy transfer may be arranged at both of the distal end and the proximal end of the freezing unit 3. Therefore, the position of the cavity 6 for preventing energy transfer depends on the types of the surgeries and the tissues to be protected. The cryoablation catheter of the present application has a simple structure, and by providing the cavity 6 for preventing energy transfer, where the freezing energy cannot be transferred, thereby resulting in a good heat insulation effect, whereby the present application can limit the release area of the freezing energy, reduce the probability of complications, and reduce the cost of treatment. Furthermore, depending on the particular requirements on the protection of the peripheral tissues of different cryoablation areas in different surgeries, the present application can provide one or more cavities 6 for preventing energy transfer, so as to further reduce the damage of the freezing energy to the peripheral tissue during the surgery, and has wide application.

The Second Embodiment

The present embodiment differs from the first embodiment in that: a supporting structure is provided between the first balloon 31 and the second balloon 32 where is adjacent to the non-treatment position, and when the first balloon 31 and the second balloon 32 are dilated, the supporting structure is able to support the cavity 6 for preventing energy transfer formed between the first balloon 31 and the second balloon 32, thereby ensuring that the shape of the cavity 6 for preventing energy transfer is stable and reliable.

Figure 2:
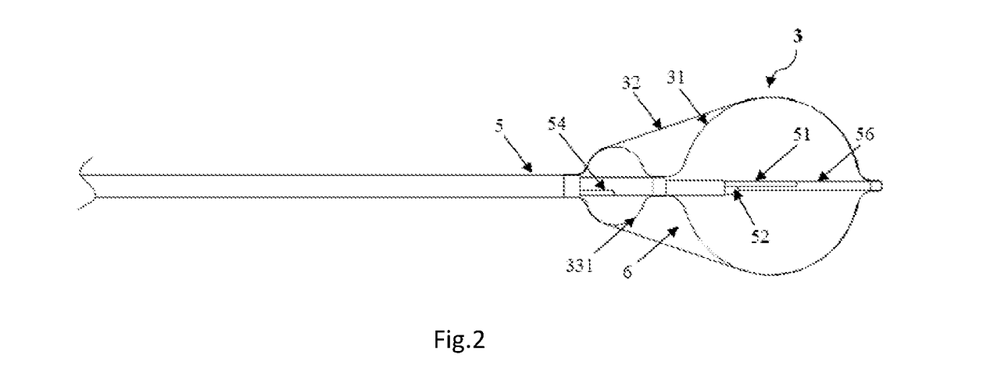
FIG. 2 is a schematic diagram of the first embodiment of the cryoablation catheter having the supporting structure of the present application.

In an embodiment, the supporting structure 33 is a balloon 331 arranged at the proximal end of the first balloon 31. As shown in FIG. 2, the catheter body 5 further comprises a balloon filling lumen 54 extending in an axial direction of the catheter body 5, and the balloon filling lumen 54 is in fluid communication with the balloon 331. During therapy, firstly a certain amount of refrigerant is injected into the first balloon 31 in order to dilate the first balloon 31 and the second balloon 32. The balloon 331 may be filled by injecting liquid/gas through the balloon filling lumen 54. Because the expansion of the balloon 331 serves to support, the vacuum heat insulation cavity is stable and reliable. Because the cavity 6 is pumped to vacuum in advance or filled with a heat insulation medium, the transferring of the freezing energy to the proximal end of the freezing unit 3 can be prevented. Then, the cryoablation therapy is started up, and a refrigerant is injected into the first balloon 31 to absorb the heat of the treatment region, and then to achieve the effect of cryoablation.

The Third Embodiment

Figure 3:
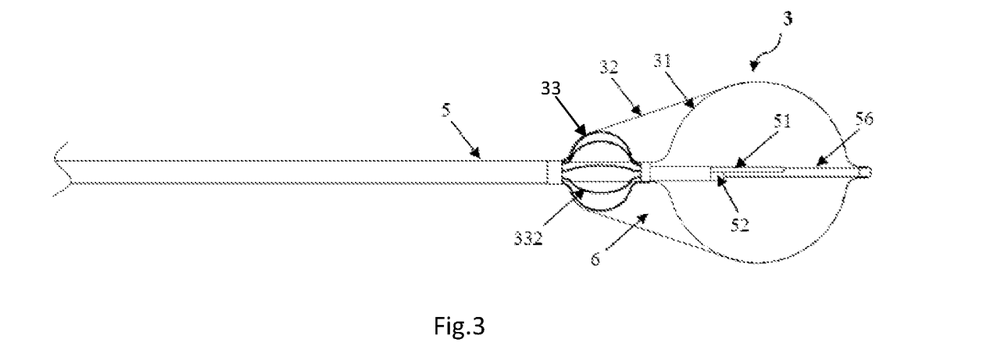
FIG. 3 is a schematic diagram of the second embodiment of the cryoablation catheter having the supporting structure of the present application.

The present embodiment differs from the second embodiment in that: as shown in FIG. 3, the supporting structure 33 may be made of one or more shape-memory-alloy wires 332 having a preset shape. The supporting structure 33, the first balloon 31 and the second balloon 32 are in a compressed state before reaching the lesion site. When the first balloon 31 has been delivered to the lesion site, the supporting structure 33 can restore the preset shape, thereby performing the supporting. Then, the cryoablation treatment is started up, and the refrigerant is injected into the first balloon 31 to absorb the heat of the treatment region, and then to achieve the effect of cryoablation. The shape-memory-alloy wires are preferably nickel-titanium wires.

Figure 16:
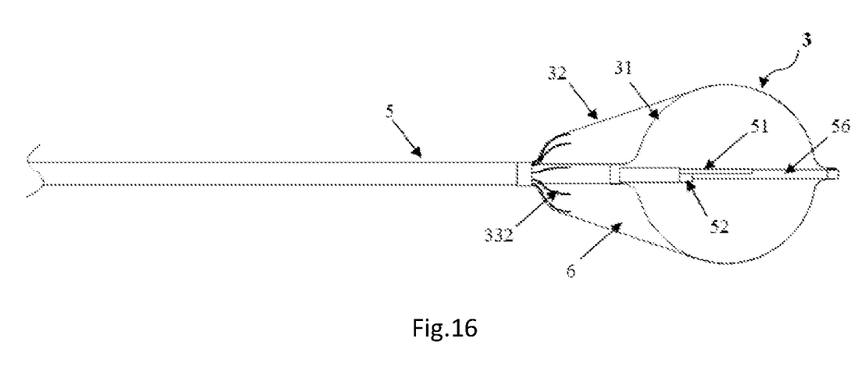
FIG. 16 is a schematic diagram of the supporting structure having preset umbrella shape of the cryoablation catheter of the present application.

In some preferable embodiments, the preset shape comprises spiral shape (as shown in FIG. 22A), cage shape (as shown in FIG. 3) or umbrella shape (as shown in FIG. 16). The shape-memory-alloy wires are shaped into shapes such as spiral shape, cage shape or umbrella shape by heat treatment.

The Fourth Embodiment

Figure 4:
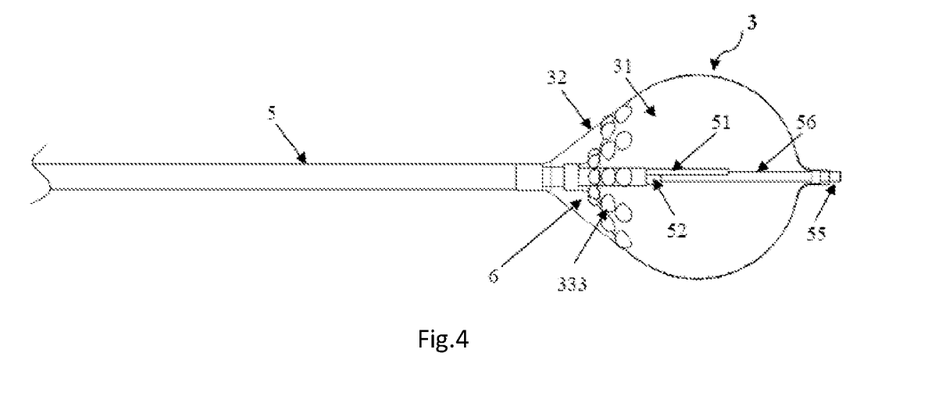
FIG. 4 is a schematic diagram of the third embodiment of the cryoablation catheter having the supporting structure of the present application.
Figure 5:
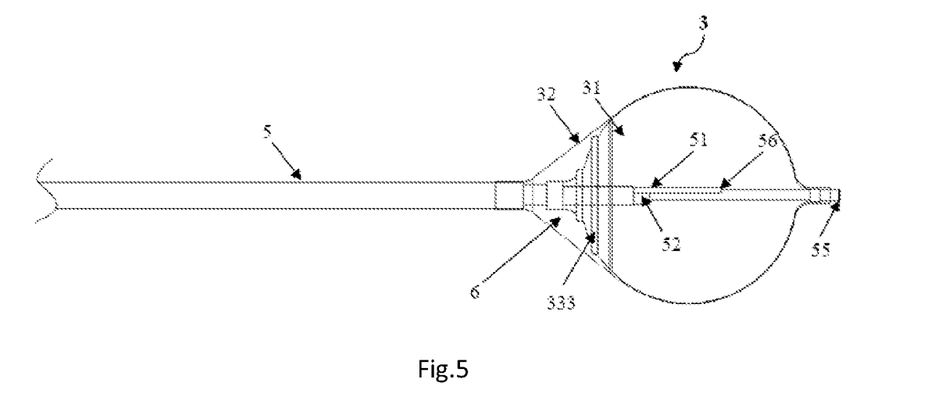
FIG. 5 is a schematic diagram of the fourth embodiment of the cryoablation catheter having the supporting structure of the present application.

The present embodiment differs from the second embodiment in that: the supporting structure 33 is a protrusion 333 arranged on the first balloon 31. The protrusion 333 is adjacent to a non-treatment region, and can serve to support action, to facilitate the forming of the cavity. As shown in FIG. 4, the protrusion 333 is of a mastoid shape, or as shown in FIG. 5, the protrusion 333 is of a thread shape. The protrusion 333 is arranged at the proximal end of the first balloon 31, and is integral with the first balloon 31. When the first balloon 31 is dilated, the protrusion 333 separates the proximal end of the first balloon 31 and the proximal end of the second balloon 32, thereby forming the cavity 6 for preventing energy transfer between the first balloon 31 and the second balloon 32. Because the space between the first balloon 31 and the second balloon 32 is pumped to vacuum in advance or filled with a heat insulation medium, at the moment a heat insulation space is formed at the proximal end of the first balloon 31, to prevent the freezing energy from being transferred to the proximal end of the freezing unit 3. When the freezing unit 3 has reached the site to be ablated, the refrigerant is injected into the first balloon 31 to absorb the heat of the treatment region, and then to achieve the effect of cryoablation.

The Fifth Embodiment

Figure 6A:
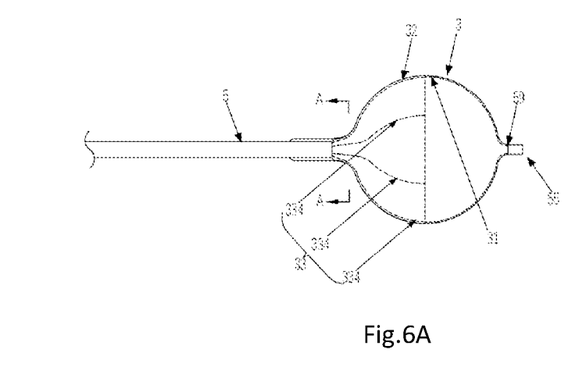
FIG. 6A is a schematic diagram of the fifth embodiment of the cryoablation catheter having the supporting structure of the present application.
Figure 6B:
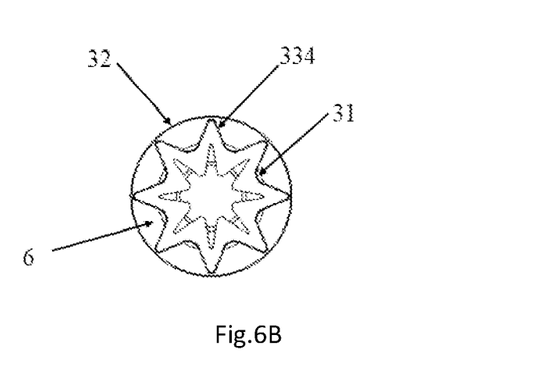
FIG. 6B is a schematic diagram of the section A-A of FIG. 6A.

The present embodiment differs from the second embodiment in that: the supporting structure 33 is one or more wrinkles 334 arranged at the proximal end and/or the distal end of the first balloon 31. The wrinkles 334 are formed by folding the first balloon 31 and changing the diameter of the first balloon 31. As shown in FIGS. 6A and 6B, the wrinkle is formed by stacking the proximal end of the first balloon 31. When the first balloon 31 is regularly folded because of diameter changing, a wrinkle of a certain height will be formed. The wrinkles 334 can serve to support the space between the first balloon and the second balloon, to prevent the second balloon 32 from touching the first balloon 31, so as to form the cavity 6 for preventing energy transfer. Because the space between the first balloon 31 and the second balloon 32 is in advance pumped to vacuum or filled with a heat insulation medium, the cavity 6 for preventing energy transfer prevents the freezing energy from being transferred to the proximal end of the freezing unit 3. When the freezing unit 3 has reached the site to be ablated, a refrigerant is injected into the first balloon 31 to absorb the heat of the treated area, so as to achieve the effect of cryoablation. Certainly, depending on different treatment sites, the wrinkle may also be arranged at the distal end of the first balloon 31.

The Sixth Embodiment

The present embodiment differs from the second embodiment in that: the supporting structure is formed by a plurality of ribbon-like or wire-like structures 335, both ends of the ribbon-like or wire-like structures 335 are fixedly connected to two ends of the second balloon 32 respectively, and when the first balloon 31 and the second balloon 32 are dilated, the ribbon-like or wire-like structures 335 are tightened to support, thereby forming the cavity 6 for preventing energy transfer between the first balloon 31 and the second balloon 32.

Figure 7A:
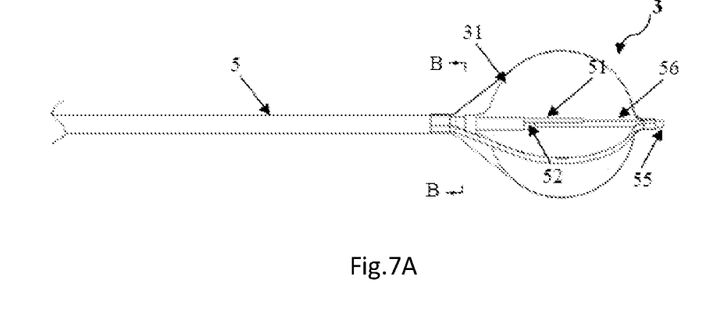
FIG. 7A is a schematic diagram of the sixth embodiment of the cryoablation catheter having the supporting structure of the present application.
Figure 7B:
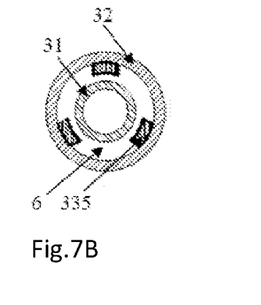
FIG. 7B is a schematic diagram of the section B-B of FIG. 7A.

As shown in FIGS. 7A and 7B, the supporting structure 33 is a flat polymer ribbon, wherein one end of it is fixed to the distal end of the second balloon 32, the other end of it is fixed to the proximal end of the second balloon 32, and both ends are located at the interior of the second balloon 32. After the first balloon 31 and the second balloon 32 being dilated, the ribbon is straightened, thereby having a certain supporting capacity. At the moment, because the space between the first balloon 31 and the second balloon 32 is in advance pumped to vacuum or filled with a heat insulation medium, the cavity 6 can prevent the energy transfer. Then, the cryoablation treatment may be started up, and a refrigerant may be injected into the first balloon 31 to absorb the heat of the treatment region, so as to achieve the effect of cryoablation.

Figure 8A:
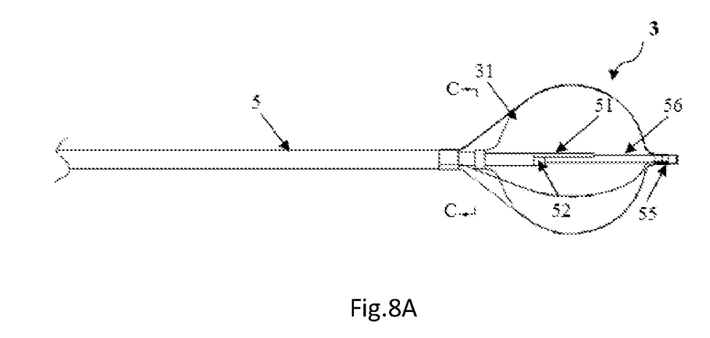
FIG. 8A is a schematic diagram of the seventh embodiment of the cryoablation catheter having the supporting structure of the present application, and Fig. B is a schematic diagram of the section C-C of FIG. 8A.
Figure 8B:
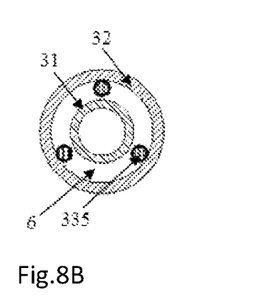

As shown in FIGS. 8A and 8B, the supporting structure is a natural silk, wherein one end of it is fixed to the distal end of the second balloon 32, the other end of it is fixed to the proximal end of the second balloon 32, and both ends are located at the interior of the second balloon 32. After the first balloon 31 and the second balloon 32 being dilated, the natural silk is straightened, thereby having a certain supporting capacity. At the moment, because the space between the first balloon 31 and the second balloon 32 is in advance pumped to vacuum or filled with a heat insulation medium, the cavity 6 can prevent the energy transfer. Then, the cryoablation treatment may be started up, and a refrigerant may be injected into the first balloon 31 to absorb the heat of the treatment region, so as to achieve the effect of cryoablation.

The Seventh Embodiment

Figure 9A:
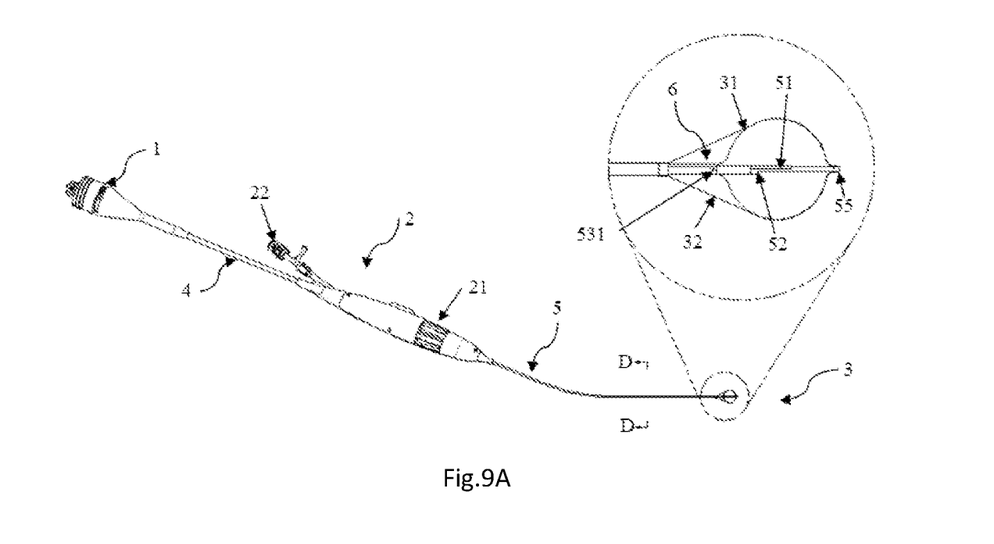
FIG. 9A is a schematic diagram of the overall structure of the cryoablation catheter having the filling and sucking lumen of the present application.
Figure 9B:
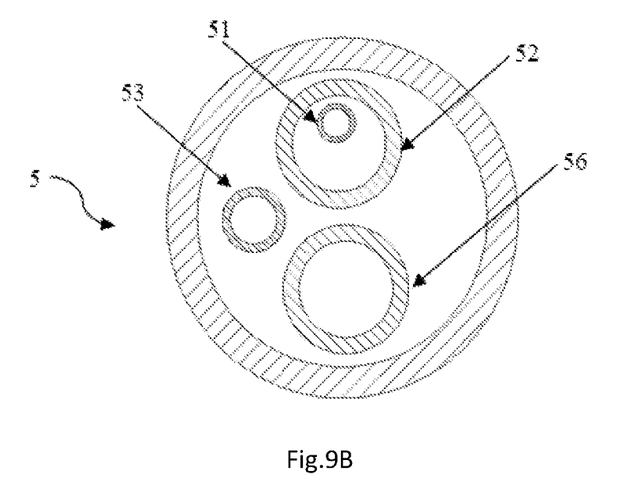
FIG. 9B is a schematic diagram of the section D-D of the catheter body of FIG. 9A.

As shown in FIGS. 9A and 9B, the cryoablation catheter of the present application comprises: a cold-source connector 1, a manipulating handle 2, a freezing unit 3, a flexible connecting pipe 4 and a catheter body 5. The catheter body 5 having a distal end and a proximal end comprises a cold-source fluid input lumen 51, a cold-source fluid output lumen 52 and a filling and sucking lumen 53 those extend in an axial direction of the catheter body 5. A filling and sucking port 531 is arranged at the distal end of the filling and sucking lumen 53. The freezing unit 3 is arranged at the distal portion of the catheter body 5, and comprises a first balloon 31 in fluid communication with the cold-source fluid input lumen 51 and the cold-source fluid output lumen 52, and a second balloon 32 arranged external to the first balloon 31. The second balloon 32 is in fluid communication with the filling and sucking lumen 53. When the first balloon 31 is dilated and the second balloon 32 is pumped to vacuum or filled with a heat insulation medium through the filling and sucking lumen 53, a heat insulation cavity 6 for preventing energy transfer is formed between the first balloon 31 and the second balloon 32. The length of the first balloon 31 is less than the length of the second balloon 32. A part of wall of the first balloon 31 and a part of wall of the second balloon 32 are fitted. The joint portion of the walls of the first balloon 31 and of the second balloon 32 is a channel for transferring the freezing energy to a treatment position.

In an embodiment, a supporting structure is arranged between the first balloon 31 and the second balloon 32. When the first balloon 31 and the second balloon 32 are dilated, the supporting structure is able to support the cavity 6 for preventing energy transfer formed between the first balloon 31 and the second balloon 32. When the second balloon 32 is pumped to vacuum through the filling and sucking lumen 53, the supporting structure can ensure that the second balloon 32 does not collapse, thereby ensuring that the shape of the cavity 6 for preventing energy transfer is stable and reliable.

The Eighth Embodiment

Figure 10:
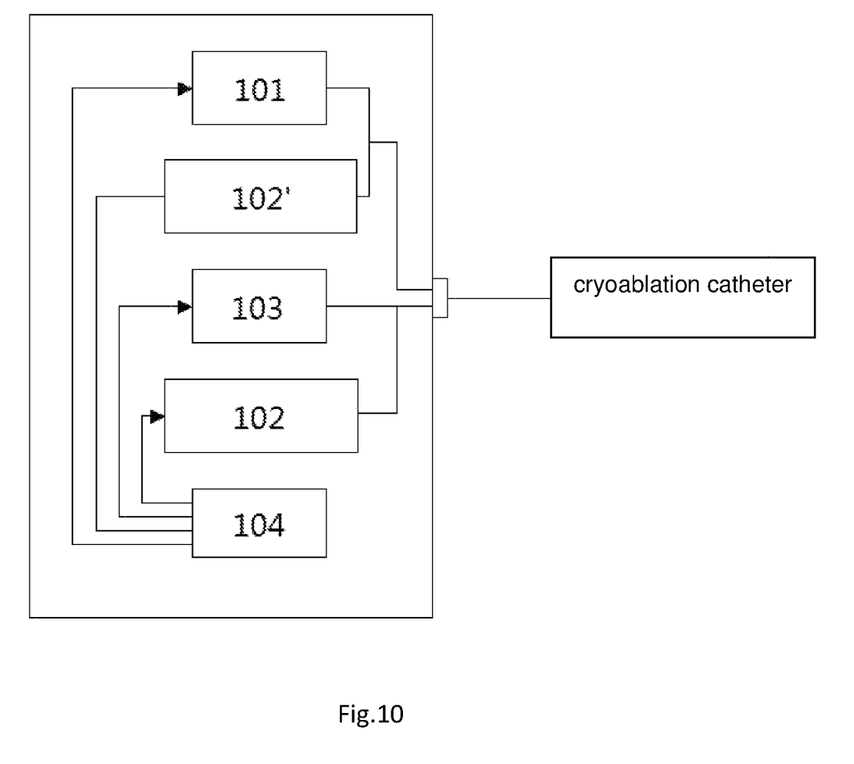
FIG. 10 is a schematic diagram of the overall structure of the cryoablation system of the present application.

As shown in FIG. 10, the cryoablation system of the present application comprises: a cryoablation catheter and a cryoablation device. The cryoablation catheter has the structure as described in the seventh embodiment. The cryoablation device comprises a heat insulation module 101, a first thawing module 102, a second thawing module 102', a freezing module 103 and a controlling system 104. The heat insulation module 101 and the second thawing module 102' are in communication with the filling and sucking lumen 53 respectively. The second thawing module 102' and the heat insulation module 101 are interlocked, wherein at a moment merely one of them can be in operation state. The freezing module 103 is in communication with the cold-source fluid input lumen 51 and the cold-source fluid output lumen 52. The first thawing module 102 is in communication with the cold-source fluid input lumen 51. The freezing module 103 and the first thawing module 102 are interlocked, wherein at a moment merely one of them can be in operation state. The controlling system 104 controls the parameters of the heat insulation module 101, the freezing module 103, the first thawing module 102 and the second thawing module 102'.

In the cryoablation stage, the freezing energy in the freezing module 103 is transferred into the first balloon 31 via the cold-source fluid input lumen 51, to dilate the first balloon 31 and the second balloon 32; and the cryoablation system fills the second balloon 32 with a heat insulation medium or pumps to vacuum the second balloon 32 by using the heat insulation module 101, so that the cavity 6 for preventing energy transfer formed between the first balloon 31 and the second balloon 32 is filled with the heat insulation medium or is pumped to a negative-pressure state, thereby preventing the freezing energy from being transferred via the cavity 6.

In the thawing stage, the first thawing module 102 and the second thawing module 102' fill a thawing fluid into the first balloon 31 and the second balloon 32 via the cold-source fluid input lumen 51 and the filling and sucking lumen 53 respectively, to enable the freezing unit 3 to be thawed rapidly. The temperature of the thawing fluid is between 0-45 degrees Celsius.

In an embodiment, the heat insulation module 101 pumps the second balloon 32 to vacuum through the filling and sucking lumen 53, thereby realizing the heat insulation function. The heat insulation module 101 is a vacuum pump.

In another embodiment, the heat insulation module 101 fills the heat insulation medium into the second balloon 32 through the filling and sucking lumen 53, thereby realizing the heat insulation function. The heat insulation module 101 is a filling pump.

The Ninth Embodiment

Figure 11:
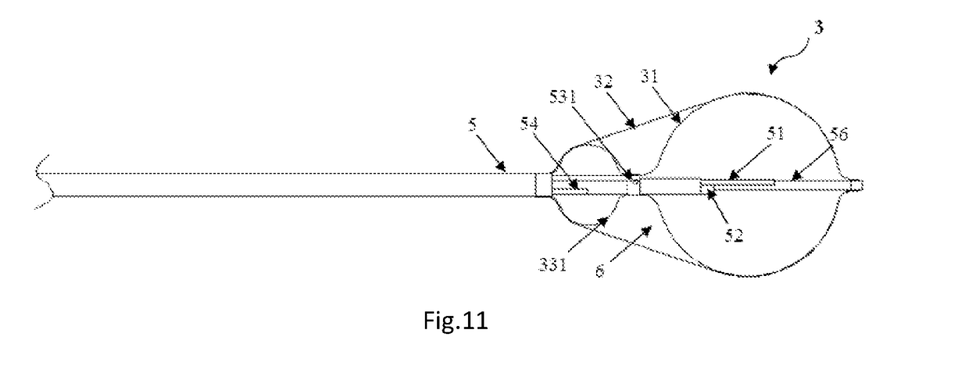
FIG. 11 is a schematic diagram of the first embodiment of the cryoablation catheter having the supporting structure of the present application.

The present embodiment differs from the eighth embodiment in that: as shown in FIG. 11, the supporting structure 33 is a balloon 331 arranged at the proximal end of the first balloon 31. The catheter body 5 further comprises a balloon filling lumen 54 extending in an axial direction of the catheter body 5, and the balloon filling lumen 54 is in fluid communication with the balloon 331. During therapy, firstly a certain amount of refrigerant is injected into the first balloon 31, so as to dilate the first balloon 31 and the second balloon 32. The balloon 331 is filled by injecting liquid/gas through the balloon filling lumen 54. The heat insulation module 101 pumps the space between the first balloon 31 and the second balloon 32 to negative pressure or fills the space between the first balloon 31 and the second balloon 32 with a heat insulation medium through the filling and sucking lumen 53 and the filling and sucking port 531. Because the dilation of the balloon 331 serves to support, the heat insulation cavity 6 is stable and reliable, to prevent the freezing energy from being transferred to the proximal end of the freezing unit 3. Then, the cryoablation treatment is started up, and a refrigerant is injected into the first balloon 31 to absorb the heat of the treated area, so as to achieve the effect of cryoablation. In the thawing stage, the second thawing module 102' fills a thawing fluid into the second balloon 32 via the filling and sucking port 531, and at the same time the first thawing unit 102 fills a thawing fluid into the first balloon 31 via the cold-source fluid input lumen 51, to accelerate the thawing of the freezing unit 3.

The Tenth Embodiment

Figure 12A:
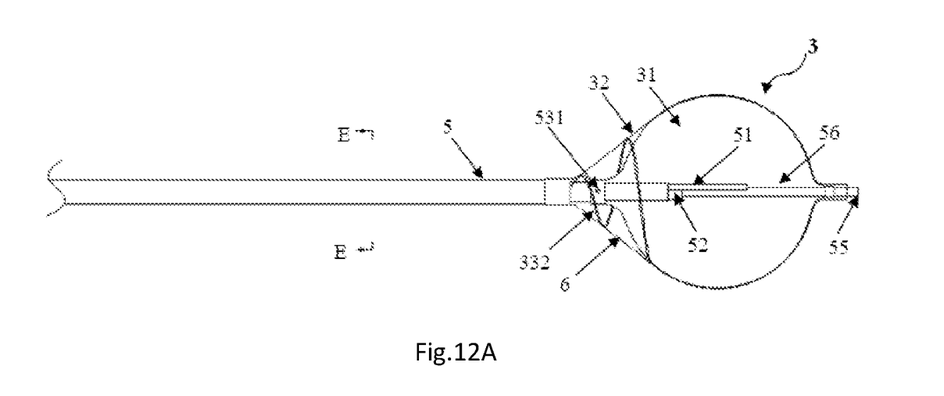
FIG. 12A is a schematic diagram of the second embodiment of the cryoablation catheter having the supporting structure of the present application.
Figure 12B:
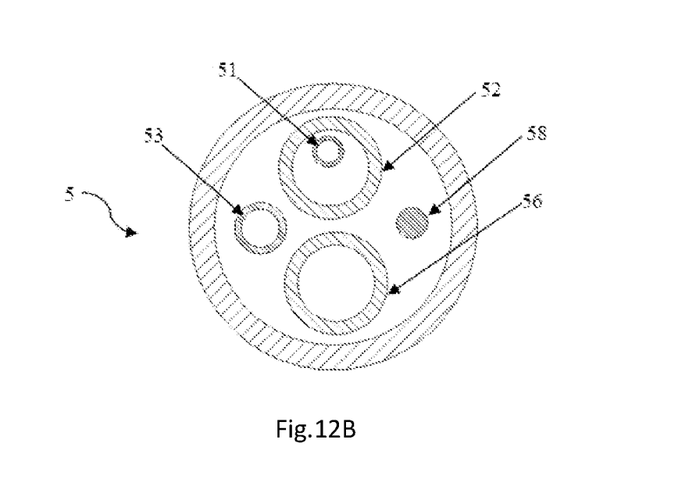
FIG. 12B is a schematic diagram of the section E-E of FIG. 12A.

The present embodiment differs from the eighth embodiment in that: as shown in FIG. 12A, the supporting structure 33 may be made of one or more shape-memory-alloy wires 332 having a preset shape. One end of the supporting structure 33 is connected to a pushing rod 58. When the first balloon 31 has been delivered to the lesion site, the supporting structure 33 is pushed to the proximal end of the first balloon 31 by the pushing rod 58, and is located between the first balloon 31 and the second balloon 32. At the same time the supporting structure 33 restores its preset shape to perform the supporting. FIG. 12B is a schematic diagram of the cross-section of the catheter body 5 of FIG. 12A. As shown in FIG. 12B, the cavity 6 between the first balloon 31 and the second balloon 32 is pumped to negative pressure or filled with a heat insulation medium through the filling and sucking port 531 of the filling and sucking lumen 53, to achieve the energy isolation. Then, the cryoablation treatment may be started up, and a refrigerant may be injected into the first balloon 31 to absorb the heat of the treatment region, to achieve the effect of cryoablation. In the thawing stage, the second thawing module 102' fills a thawing fluid into the second balloon 32 via the filling and sucking port 531 of the filling and sucking lumen 53, and at the same time the first thawing unit 102 fills a thawing fluid into the first balloon 31 via the cold-source fluid input lumen 51, to accelerate the thawing of the freezing unit 3. The shape-memory-alloy wires are preferably nickel-titanium wires. In some preferable embodiments, the preset shape comprises spiral shape, cage shape or umbrella shape. The shape-memory-alloy wires are shaped into shapes such as spiral shape, cage shape or umbrella shape by heat treatment. During the cryoablation catheter is delivered to the lesion site, the supporting structure 33 is compressed within the catheter body 5. When the supporting structure 33 has been pushed by the pushing handle into the space between the first balloon 31 and the second balloon 32, the supporting structure 33 made of the shape-memory-alloy wires 332 restores the reset shape obtained by heat treatment.

The Eleventh Embodiment

The present embodiment differs from the eighth embodiment in that: the supporting structure is formed by a plurality of ribbon-like or wire-like structures 335, and both ends of the ribbon-like or wire-like structures 335 are fixedly connected to two ends of the second balloon 32 respectively, and when the first balloon 31 is dilated, the ribbon-like or wire-like structures 335 are tightened to provide supporting, thereby forming the cavity 6 for preventing energy transfer between the first balloon 31 and the second balloon 32.

Figures 13A, 13B:
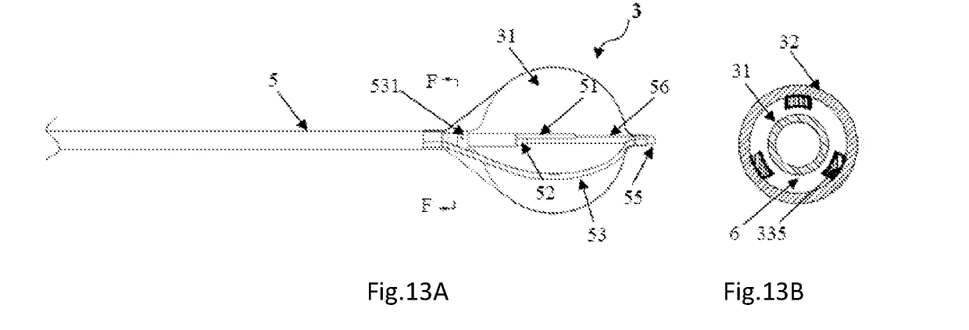
FIG. 13A is a schematic diagram of the third embodiment of the cryoablation catheter having the supporting structure of the present application.
FIG. 13B is a schematic diagram of the section F-F of FIG. 13A.

As shown in FIGS. 13A and 13B, the supporting structure 33 is a flat polymer ribbon, wherein one end of it is fixed to the distal end of the second balloon 32, the other end of it is fixed to the proximal end of the second balloon 32, and both ends are located at the interior of the second balloon 32. When the first balloon 31 and the second balloon 32 are dilated, the ribbon is straightened, thereby having a certain supporting capacity. At the moment this region is pumped to negative pressure or filled with a heat insulation medium, to form the energy isolation. Then, the cryoablation treatment may be started up, and a refrigerant may be injected into the first balloon 31 to absorb the heat of the treated area, so as to achieve the effect of cryoablation. In the thawing stage, the second thawing module 102' fills a thawing fluid into the second balloon 32 via the filling and sucking port 531, and at the same time the first thawing unit 102 fills a thawing fluid into the first balloon 31 via the cold-source fluid input lumen 51, to accelerate the thawing of the freezing unit 3.

Figure 14A:
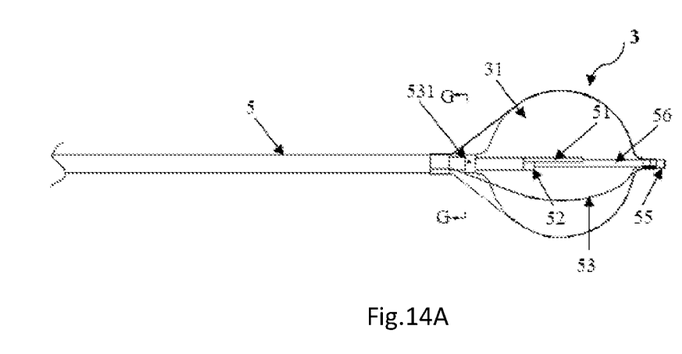
FIG. 14A is a schematic diagram of the fourth embodiment of the cryoablation catheter having the supporting structure of the present application.
Figure 14B:
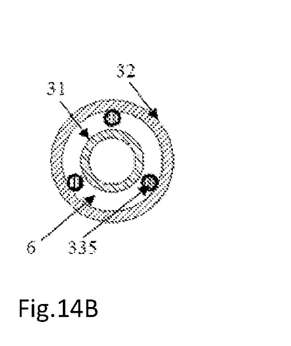
FIG. 14B is a schematic diagram of the section G-G of FIG. 14A.

As shown in FIGS. 14A and 14B, the supporting structure is a natural silk, wherein one end of it is fixed to the distal end of the second balloon 32, the other end of it is fixed to the proximal end of the second balloon 32, and both ends are located at the interior of the second balloon 32. When the first balloon 31 and the second balloon 32 are dilated, the natural silk is straightened, thereby having a certain supporting capacity. At the moment the region is pumped to negative pressure or filled with a heat insulation medium, to form the energy isolation. Then, the cryoablation treatment may be started up, and a refrigerant may be injected into the first balloon 31 to absorb the heat of the treated area, so as to achieve the effect of cryoablation.

Figure 15:
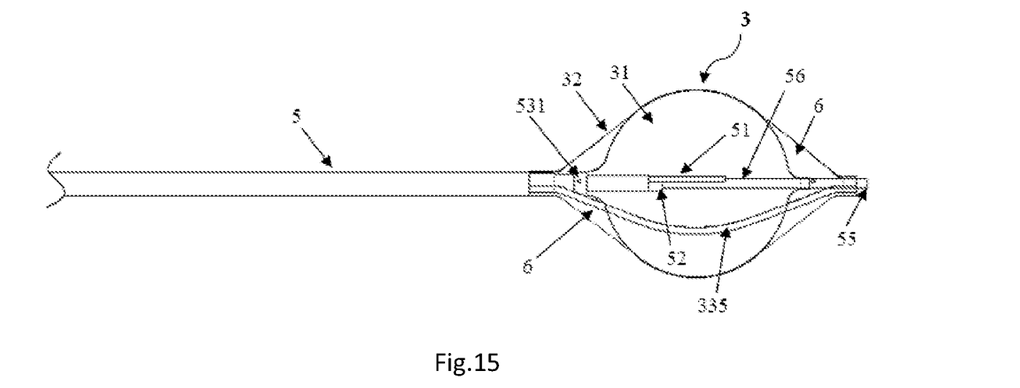
FIG. 15 is a schematic diagram of the fifth embodiment of the cryoablation catheter having the supporting structure of the present application.

As shown in FIG. 15, the supporting structure 33 is a flat polymer ribbon 335, wherein one end of it is fixed to the distal end of the second balloon 32, the other end of it is fixed to the proximal end of the second balloon 32, and both ends are located at the interior of the second balloon 32. When the first balloon 31 and the second balloon 32 are dilated, the ribbon is straightened, thereby having a certain supporting capacity. The cavity 6 for preventing energy transfer is formed at both of the distal end and the proximal end of the first balloon 31. At the moment the region is pumped to negative pressure or filled with a heat insulation medium, to prevent the freezing energy from being transferred to the two ends of the freezing unit 3. Then, the cryoablation treatment may be started up, and a refrigerant may be injected into the first balloon 31 to absorb the heat of the treated area, so as to achieve the effect of cryoablation.

Finally, it should be noted that, the above are merely preferable embodiments of the present application, and are not limiting the present disclosure. Any modifications, equivalent substitutions and improvements that are made within the spirit and principle of the present application should be included in the protection scope of the present application.

What is claimed is:

1. A cryoablation catheter comprising:
   a catheter body, the catheter body comprises a cold-source fluid input lumen and a cold-source fluid output lumen both extending in an axial direction of the catheter body; and
   a freezing unit arranged at a distal portion of the catheter body, the freezing unit comprises a first balloon in fluid communication with the cold-source fluid input lumen and the cold-source fluid output lumen, and a second balloon arranged external to the first balloon, and a length of the first balloon is less than a length of the second balloon, an area between the first balloon and the second balloon is a sealed space, and the sealed space is configured to be pumped to a vacuum state in advance, a part of a wall of the first balloon and a part of a wall of the second balloon are fitted, and a joint portion of the walls of the first balloon and of the second balloon is a channel for transferring freezing energy to a treatment position, the first balloon and the second balloon have a same endpoint at the distal portion of the catheter body;
   when the first balloon and the second balloon are dilated, a cavity for preventing energy transfer is formed between the first balloon and the second balloon, to prevent energy transfer in a space of the freezing unit corresponding to the cavity;
   wherein a supporting structure is provided between the first balloon and the second balloon, and when the first balloon and the second balloon are dilated, the supporting structure is configured to provide support between the first balloon and the second balloon to ensure the cavity to be formed for preventing energy transfer, and the supporting structure is located in the cavity;
   wherein the supporting structure is a wrinkle set in the first balloon that extends either from a proximal end of the first balloon to a middle portion of the first balloon, or from a distal end of the first balloon to the middle portion of the first balloon;
   wherein the wrinkle is formed by folding part of the first balloon and changing a diameter of the first balloon.

2. The cryoablation catheter according to claim 1, wherein the cavity is pre-filled with a heat insulation fluid, so as to block energy transfer inside the cavity.

3. A cryoablation system comprising:
   a cryoablation catheter, the cryoablation catheter comprises a catheter body and a freezing unit arranged at a distal portion of the catheter body, and the catheter body comprises a cold-source fluid input lumen, a cold-source fluid output lumen and a filling and sucking lumen, and they extend in an axial direction of the catheter body; and the freezing unit comprises a first balloon in fluid communication with the cold-source fluid input lumen and the cold-source fluid output lumen, and a second balloon arranged external to the first balloon, and the second balloon is in communication with the filling and sucking lumen, a length of the first balloon is less than a length of the second balloon, an area between the first balloon and the second balloon is a sealed space, and the sealed space is configured to be pumped to a vacuum state in advance, a part of a wall of the first balloon and a part of a wall of the second balloon are fitted, and a joint portion of the walls of the first balloon and of the second balloon is a channel for transferring freezing energy to a treatment position, the first balloon and the second balloon have a same endpoint at the distal portion of the catheter body;
   wherein a supporting structure is provided between the first balloon and the second balloon, and when the first balloon and the second balloon are dilated, a cavity for preventing energy transfer is formed between the first balloon and the second balloon, and the supporting structure is configured to provide support between the first balloon and the second balloon to ensure the cavity to be formed for preventing energy transfer, and the supporting structure is located in the cavity;
   wherein the supporting structure is a wrinkle set in the first balloon that extends either from a proximal end of the first balloon to a middle portion of the first balloon, or from a distal end of the first balloon to the middle portion of the first balloon;
   wherein the wrinkle is formed by folding part of the first balloon and changing a diameter of the first balloon; and
   a cryoablation device, the cryoablation device comprises a heat insulation module and a second thawing module that are in communication with the filling and sucking lumen, a freezing module that is in communication with the cold-source fluid input lumen and the cold-source fluid output lumen, a first thawing module that is in communication with the cold-source fluid input lumen, and a controlling system that controls parameters of the heat insulation module, the freezing module, the first thawing module and the second thawing module.

4. The cryoablation system according to claim 3, wherein the heat insulation module is a filling pump.

5. The cryoablation system according to claim 3, wherein the heat insulation module is a vacuum pump.

* * * * *